(12) United States Patent
Vandenbark et al.

(10) Patent No.: US 10,316,075 B2
(45) Date of Patent: *Jun. 11, 2019

(54) RECOMBINANT POLYPEPTIDES COMPRISING MHC CLASS II α1 DOMAINS

(71) Applicants: Oregon Health & Science University, Portland, OR (US); The United States of America as Represented by the Department of Veterans Affairs, Washington, DC (US)

(72) Inventors: Arthur A. Vandenbark, Portland, OR (US); Roberto Meza-Romero, Hillsboro, OR (US); Gil Benedek, Portland, OR (US); Gregory G. Burrows, Portland, OR (US)

(73) Assignees: Oregon Health & Science University, Portland, OR (US); The United States of America as Represented by the Department of Veterans Affairs, Washington, DC (US)

( * ) Notice: Subject to any disclaimer, the term of this patent is extended or adjusted under 35 U.S.C. 154(b) by 489 days.

This patent is subject to a terminal disclaimer.

(21) Appl. No.: 14/506,502

(22) Filed: Oct. 3, 2014

(65) Prior Publication Data

US 2015/0098956 A1 Apr. 9, 2015

Related U.S. Application Data

(60) Provisional application No. 61/886,261, filed on Oct. 3, 2013.

(51) Int. Cl.
| | |
|---|---|
| *A61K 39/00* | (2006.01) |
| *C07K 14/705* | (2006.01) |
| *C07K 14/74* | (2006.01) |
| *A61K 39/008* | (2006.01) |
| *C07H 21/04* | (2006.01) |

(52) U.S. Cl.
CPC ........ *C07K 14/705* (2013.01); *A61K 39/0008* (2013.01); *C07K 14/70539* (2013.01); *A61K 2039/605* (2013.01); *A61K 2039/627* (2013.01); *C07K 2319/35* (2013.01)

(58) Field of Classification Search
None
See application file for complete search history.

(56) References Cited

U.S. PATENT DOCUMENTS

| | | | |
|---|---|---|---|
| 7,741,057 B2 | 6/2010 | Bucala et al. | |
| 8,377,447 B2 | 2/2013 | Burrows et al. | |
| 8,491,913 B2 | 7/2013 | Offner et al. | |
| 8,895,018 B2 * | 11/2014 | Vandenbark | A61K 39/0007 424/185.1 |
| 9,359,425 B2 * | 6/2016 | Vandenbark | A61K 39/0007 |
| 2004/0127408 A1 | 7/2004 | Mozes | |
| 2005/0260222 A1 | 11/2005 | Gupta et al. | |
| 2011/0318380 A1 | 12/2011 | Brix et al. | |
| 2012/0195291 A1 | 8/2012 | Loftis et al. | |
| 2012/0276127 A1 | 11/2012 | Adamus et al. | |
| 2013/0190221 A1 | 7/2013 | Burrows et al. | |
| 2015/0099706 A1 | 4/2015 | Offner-Vandenbark et al. | |

FOREIGN PATENT DOCUMENTS

| | | |
|---|---|---|
| WO | WO 96/40944 | 12/1996 |
| WO | WO 98/06749 | 2/1998 |
| WO | WO 99/21572 | 5/1999 |
| WO | WO 02/087613 | 11/2002 |
| WO | WO 2006/102170 | 9/2006 |
| WO | WO 2008/094510 | 8/2008 |
| WO | WO 2009/117706 | 9/2009 |
| WO | WO 2009/117710 | 9/2009 |
| WO | WO 2011/147894 | 12/2011 |
| WO | WO 2012/031258 | 3/2012 |
| WO | WO 2012/103365 | 8/2012 |
| WO | WO 2013/103816 | 7/2013 |

OTHER PUBLICATIONS

Basha et al (Nature Immunol. 2012, 13(3): 237-246).*
ClinicalTrials.gov (clinicaltrials.gov/ct2/show/NCT00411723, 2009).*
Johnson, C (abc7news.com/archive/581449, 2007).*
Christodoulou (Basic Laboratory Practices, structbio.vanderbilt.edu/chazin/wisdom/labpro/thrombin.html, 2000).*
Medical News Today (2017) (Year: 2018).*
DrSears.com (Year: 2018).*
Benedek et al., "A novel HLA-DRα1-MOG-35-55 construct treats experimental stroke," *Metab. Brain Dis.*, vol. 29, pp. 37-45, 2014.
Lawrance et al., "Transgenic HLA-DRα faithfully reconstitutes IE-controlled immune functions and induces cross-tolerance to Eα in Eα° mutant mice," *Cell*, vol. 58, pp. 583-594, 1989.
Vandenbark et al., "A novel regulatory pathway for autoimmune disease: Binding of partial MHC class II constructs to monocytes reduces CD74 expression and induces both specific and bystander T-cell tolerance," *J. Autoimmunity*, vol. 40, pp. 95-110, 2013.
Akiyoshi et al., "Recombinant T cell receptor ligands improve outcome after experimental cerebral ischemia," *Transl. Stroke Res.* vol. 2, No. 3, pp. 404-410, 2011.
Banerjee et al., "Phenotypic changes in immune cell subsets reflect increased infarct volume in male vs. female mice," *Transl. Stroke Res.* vol. 4, No. 5, pp. 554-563, 2013 (19 pages).

(Continued)

*Primary Examiner* — G. R. Ewoldt
*Assistant Examiner* — Marianne DiBrino
(74) *Attorney, Agent, or Firm* — Klarquist Sparkman, LLP (57) ABSTRACT

Recombinant polypeptides comprising a DRα1 domain, an antigenic peptide, and a linker sequence are disclosed. The linker sequence comprises a first glycine-serine spacer, a thrombin cleavage site and a second glycine-serine spacer. Further disclosed are pharmaceutical compositions comprising the recombinant polypeptides, methods of treating inflammatory disease using said pharmaceutical compositions, and expression constructs comprising nucleic acids that encode the recombinant polypeptides.

8 Claims, 6 Drawing Sheets

Specification includes a Sequence Listing.

(56) References Cited

OTHER PUBLICATIONS

Binsky et al., "IL-8 Secreted in a Macrophage Migration-Inhibitory Factor- and CD74-Dependent Manner Regulates B Cell Chronic Lymphocytic Leukemia Survival," *PNAS* vol. 104, No. 33, pp. 13408-13413, 2007.
Burrows et al., "Design, engineering and production of functional single-chain T cell receptor ligands," *Protein Engineering*, vol. 12, No. 9, pp. 771-778, 1999.
Burrows et al., "Rudimentary TCR Signaling Triggers Default IL-10 Secretion by Human Th1 Cells," *J. Immunol.*, vol. 167, pp. 4386-4395, 2001.
Chang et al., "Design, Engineering, and Production of Human Recombinant T Cell Receptor Ligands Derived from Human Leukocyte Antigen DR2," *J. Biol. Chem.*, vol. 276, No. 26, pp. 24170-24176, 2001.
Dziennis et al., "Therapy with recombinant T-cell receptor ligand reduces infarct size and infiltrating inflammatory cells in brain after middle cerebral artery occlusion in mice," *Metab. Brain Dis.* vol. 26, pp. 123-133, 2011.
Fissolo et al. "Naturally Presented Peptides on Major Histocompatibility Complex I and II Molecules Eluted from Central Nervous System of Multiple Sclerosis Patients," *Mol. Cell. Proteomics*, vol. 8, pp. 2090-2101, 2009.
Fontenot et al., "Recombinant HLA-DP2 Binds Beryllium and Tolerizes Beryllium-Specific Pathogenic CD4 $^+$ T Cells," *J. Immunol.*, vol. 177, pp. 3874-3883, 2006.
Gore et al., "Macrophage Migration Inhibitory Factor Induces B Cell Survival by Activation of a CD74-CD44 Receptor Complex," *J. Biol. Chem.* vol. 283, No. 5, pp. 2784-2792, 2008.
Huan et al. "Rationally designed mutations convert complexes of human recombinant T cell receptor ligands into monomers that retain biological activity," *J. Chem. Technol. Biotechnol.*, vol. 80, pp. 2-12, 2005.
Hurn et al. "T- and B-cell deficient mice with experimental stroke have reduced lesion size and inflammation," *J. Cereb. Blood Flow Metab.* vol. 27, pp. 1798-1805, 2007.
Lapter et al., "A Role for the B-Cell CD74/Macrophage Migration Inhibitory Factor Pathway in the Immunomodulation of Systemic Lupus Erythematosus by a Therapeutic Tolerogenic Peptide," *Immunol.* vol. 132, pp. 87-95, 2010.
Leng et al., "MIF Signal Transduction Initiated by Binding to CD74," *J. Exp. Med.* vol. 197, No. 11, pp. 1467-1476, 2003.
Liu et al., "An Ancient Balanced Polymorphism in a Regulatory Region of Human Major Histocompatibility Complex is Retained in Chinese Minorities but Lost Worldwide," *Am. J. Hum. Genet.* vol. 78, pp. 393-400, 2006.
Mungall et al., "The DNA sequence and analysis of human chromosome 6," *Nature* vol. 425, No. 6960, pp. 805-811, 2003.
Offner et al., "Treatment of Passive Experimental Autoimmune Encephalomyelitis in SJL Mice with a Recombinant TCR Ligand Induces IL-13 and Prevents Axonal Injury," *J. Immunol.*, vol. 175, pp. 4103-4111, 2005.
Offner et al. "Experimental stroke induces massive, rapid activation of the peripheral immune system," *J. Cereb. Blood Flow Metab.* vol. 26, pp. 654-665, 2006.
Offner et al. "Splenic atrophy in experimental stroke is accompanied by increased regulatory T cells and circulating macrophages," *J. Immunol.* vol. 176, pp. 6523-6531, 2006.
Pan et al., "Novel humanized recombinant T cell receptor ligands protect the female brain after experimental stroke," *Transl. Stroke Res.* vol. 5, No. 5, pp. 577-585, 2014.
Ren et al. "CD4+FoxP3+ regulatory T-cells in cerebral ischemic stroke," *Metab. Brain Dis.* vol. 26, pp. 87-90, 2011 (NIH Public Access Author Manuscript, 6 pages).
Sinha et al. "A Promising Therapeutic Approach for Multiple Sclerosis: Recombinant T-Cell Receptor Ligands Modulate Experimental Autoimmune Encephalomyelitis by Reducing Interleukin-17 Production and Inhibiting Migration of Encephalitogenic Cells into the CNS," *J. Neurosci.*, vol. 27, pp. 12531-12539, 2007.
Sinha et al. "RTL551 Treatment of EAE Reduces CD226 and T-bet+ CD4 T Cells in Periphery and Prevents Infiltration of T-bet+ IL-17, IFN-γ Producing T Cells into CNS," *PLoS ONE*, vol. 6, e21868, 2011 (12 pages).
Starlets et al., "Cell-surface CD74 initiates a signaling cascade leading to cell proliferation and survival," *Blood* 107:4807-4816, 2006.
Subramanian et al. "Recombinant T Cell Receptor Ligand Treats Experimental Stroke," *Stroke*, vol. 40, pp. 2539-2545, 2009.
UNIPROT Accession No. F8W032, 2013 (3 pages).
UNIPROT Accession No. Q29ZN1, 2006 (1 page).
Vandenbark et al., "Recombinant TCR Ligand Induces Tolerance to Myelin Oligodendrocyte Glycoprotein 35-55 Peptide and Reverses Clinical and Histological Signs of Chronic Experimental Autoimmune Encephalomyelitis in HLA-DR2 Transgenic Mice," *J. Immunol.*, vol. 171, pp. 127-133, 2003.
Chichili et al., "Linkers in the structural biology of protein-protein interactions," *Protein Science*, 22: 153-167, 2013.

\* cited by examiner

RECOMBINANT POLYPEPTIDES COMPRISING MHC CLASS II α1 DOMAINS

CROSS REFERENCE TO RELATED APPLICATIONS

This claims the benefit of U.S. Provisional Application No. 61/886,261, filed Oct. 3, 2013, which is incorporated herein by reference in its entirety.

ACKNOWLEDGEMENT OF GOVERNMENT SUPPORT

This invention was made with the support of the United States government under the terms of Grant Number 5RO1 NS047661 awarded by the National Institutes of Health and a Merit Review Grant awarded by the Veterans Administration. The United States government has certain rights to this invention.

FIELD

This disclosure relates to recombinant therapeutic proteins, particularly partial MHC molecules useful in the treatment of inflammatory disease.

BACKGROUND

The initiation of an immune response against a specific antigen in mammals is brought about by presentation of that antigen to T-cells. An antigen is presented to T cells in the context of a major histocompatibility complex (MHC). MHCs are located on the surface of antigen presenting cells (APCs); the three-dimensional structure of MHCs includes a groove or cleft into which the presented antigen fits. When an appropriate receptor on a T-cell interacts with the MHC/antigen complex on an APC in the presence of necessary co-stimulatory signals, the T-cell is stimulated, triggering various aspects of the well-characterized cascade of immune system activation events, including induction of cytotoxic T-cell function, induction of B-cell function, and stimulation of cytokine production.

The pathology of multiple sclerosis is characterized by an abnormal immune response directed against the central nervous system. In particular, T-lymphocytes reactive against myelin antigens are believed to initiate an inflammatory response within the central nervous system. The resultant inflammatory response includes recruited T-lymphocytes, activated macrophages, B-lymphocytes and plasma cells. Soluble mediators released by these inflammatory cells result in demyelination and axonal degeneration. Similarly, inflammatory responses in many autoimmune disorders result in tissue damage, often of a progressive nature. Despite recent progress, effective treatments of autoimmune and inflammatory disorders are still needed.

Major histocompatibility complex (MHC) class II α1 domain polypeptides have proven useful in treatment of multiple sclerosis (WO 2013/103816, which is incorporated by reference herein).

SUMMARY

Disclosed herein is an MHC class II α1 domain polypeptide comprising a MOG-35-55 peptide conjugated to the MHC class II α1 domain via a linker. This construct results in an unexpected level of stability to the secondary structure of the DRα1 domain and unexpectedly improved efficacy in the treatment of inflammatory disease relative to an MHC class II α1 domain polypeptide lacking the MOG-35-55 peptide.

Disclosed herein is a recombinant polypeptide comprising a DRα1 domain, an antigenic peptide, and a linker sequence, the linker sequence comprising a first glycine serine-spacer, a thrombin cleavage site, and a second glycine-serine spacer. In some examples the antigenic peptide is MOG-35-55, such as SEQ ID NO:1 or a homolog thereof.

Additionally, disclosed herein are pharmaceutical compositions comprising an effective dose of the disclosed recombinant polypeptides and a pharmaceutically acceptable carrier. In some examples, the effective dose is at least 5 mg/kg.

Further disclosed herein are methods of treating inflammatory disorders such as multiple sclerosis (or its mouse model, EAE) comprising administering the disclosed pharmaceutical compositions (such as a composition including the polypeptide of SEQ ID NO: 1) to a subject that is suffering from the inflammatory disorder.

Also disclosed are expression constructs comprising a nucleic acid that encodes SEQ ID NO: 1 or a homolog thereof and cell lines comprising that expression construct. In some examples the expression construct includes the nucleic acid sequence of SEQ ID NO: 2.

BRIEF DESCRIPTION OF THE DRAWINGS

FIGS. 4A-4D are a set of digital images of specimens from the experiment depicted in FIG. 2.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 2, 2014, and is 2334 bytes, which is incorporated by reference herein.

SEQ ID NO: 1 is a protein sequence of an exemplary human DRα1 polypeptide comprising a murine MOG-35-55 peptide and a linker, wherein the linker is covalently linked to the N-terminus of the DRα1 polypeptide and the MOG-35-55 peptide is linked to the N-terminus of the linker.

SEQ ID NO: 2 is an exemplary nucleic acid sequence encoding the protein of SEQ ID NO: 1.

DETAILED DESCRIPTION

Disclosed herein is a chimeric protein construct comprising: a) a human DRα1 polypeptide, b) an antigenic peptide, and c) peptide linker. The antigenic peptide may be any antigenic peptide, such as human MOG-35-55 and mouse MOG-35-55. The peptide linker comprises a first glycine-serine spacer, a thrombin cleavage site and a second glycine-serine spacer. The linker is covalently bound to the amino terminus of the DRα1 polypeptide and to the carboxyl terminus of a MOG-35-55 peptide. The MOG-35-55 peptide may be mouse MOG-35-55 or human MOG-35-55.

The protein was purified through a method described in International Pat. Publ. No. WO 2013/103816, which is incorporated by reference herein.

Also disclosed herein are pharmaceutical compositions comprising the chimeric protein construct described above and a pharmaceutically acceptable carrier. Such pharmaceutical compositions may be formulated for any appropriate route of administration by one of ordinary skill in the art.

Additionally disclosed herein are methods of treating autoimmune diseases such as multiple sclerosis, which is assessed using the experimental autoimmune encephalomyelitis (EAE) model in mice. In some examples, the disclosed methods include administering an effective amount of a disclosed polypeptide (for example, SEQ ID NO: 1) to a subject having or at risk of multiple sclerosis.

The disclosed compositions (exemplified by SEQ ID NO: 1) have unexpected advantages over previously described compositions solely comprising a DRα1 polypeptide. Addition of the antigenic peptide has unexpected effects on the secondary structure of the DRα1 domain. Furthermore, these compositions are unexpectedly more potent than compositions made solely of a DRα1 polypeptide in an EAE model. Finally, the disclosed compositions more potently inhibit CD74 expression than compositions made solely of a DRα1 polypeptide.

I. Abbreviations

APC antigen presenting cell
CDI cumulative disease index
EAE experimental autoimmune encephalomyelitis
HLA human leukocyte antigen
MBP myelin basic protein
MIF macrophage migration inhibitory factor
MHC major histocompatibility complex
MOG myelin oligodendrocyte glycoprotein
PBMC peripheral blood mononuclear cell
pMHC partial MHC (β1α1) polypeptide
PLP proteolipid protein
RTL recombinant T cell receptor ligand

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. All GenBank Accession numbers mentioned herein are incorporated by reference in their entirety as present in GenBank on Oct. 2, 2013. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 8 amino acids (such as about 8-50 or 8-23 amino acids) in a unique spatial conformation. Methods of determining spatial conformation of epitopes include, for example, x-ray crystallography and two-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. A tissue-specific antigen may be expressed by more than one tissue, such as, but not limited to, an antigen that is expressed in the central or peripheral nervous system.

CD74: Also known as CD74 molecule, major histocompatibility complex, class II invariant chain or Ii. CD74 is a chaperone regulating antigen presentation. It is also a cell surface receptor for macrophage migration inhibitory factor (MIF). Nucleic acid and protein sequences for CD74 are publicly available. For example, GenBank Accession Nos. NM_001025158, NM_004355, and NM_001025159 disclose exemplary human CD74 nucleic acid sequences, and GenBank Accession Nos. NP_001020329, NP_004346, and NP_001020330 disclose exemplary human CD74 amino acid sequences. Similarly, GenBank Accession Nos. NM_001042605 and NM_010545 disclose exemplary mouse CD74 nucleic acid sequences, and GenBank Accession Nos. NP_001036070 and NP_034675 disclose exemplary mouse CD74 amino acid sequences. Each of these sequences is incorporated herein by reference as present in GenBank on Oct. 2, 2013.

Conservative variants: A substitution of an amino acid residue for another amino acid residue having similar biochemical properties. "Conservative" amino acid substitutions are those substitutions that do not substantially affect or decrease an activity of an MHC Class II polypeptide, such as an MHC class II α1 polypeptide. A polypeptide can include one or more amino acid substitutions, for example 1-10 conservative substitutions, 2-5 conservative substitutions, 4-9 conservative substitutions, such as 1, 2, 5 or 10 conservative substitutions. Specific, non-limiting examples of a conservative substitution include the following:

| Original Amino Acid | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Control: A "control" refers to a sample or standard used for comparison with an experimental sample. In some embodiments, the control is a sample obtained from a healthy subject or population of healthy subjects. In other embodiments, the control is a historical control or standard reference value or range of values (such as a previously tested control sample, such as a group of samples that represent baseline or normal values, such as the level of CD74 expression or activity in healthy subjects). In further examples, the control is from a subject prior to treatment (such as CD74 expression or activity level prior to treatment with an MHC class II β1α1 polypeptide or an MHC class II α1 domain polypeptide).

Domain: A discrete part of an amino acid sequence of a polypeptide or protein that can be equated with a particular function. For example, the α and β polypeptides that constitute a MHC class II molecule are each recognized as having two domains, α1, α2 and β1, β2, respectively. The various domains are typically joined by linking amino acid sequences. In one embodiment, the entire domain sequence is included in a recombinant molecule by extending the sequence to include all or part of the linker or the adjacent domain. For example, when selecting the α1 domain of an MHC class II molecule, the selected sequence may extend from amino acid residue number 1 of the α chain, through the entire α1 domain to amino acid 84 at the carboxy terminus of the α1 domain. The precise number of amino acids in the various MHC molecule domains varies depending on the species of mammal, as well as between classes of genes within a species. The selection of a sequence for use in a recombinant molecule requires maintenance of the domain function rather than a precise structural definition based on the number of amino acids. One of ordinary skill in the art will appreciate that domain function may be maintained even if somewhat less than the entire amino acid sequence of the selected domain is utilized. For example, a number of amino acids at either the amino or carboxy termini of the α1 domain may be omitted without affecting domain function. The functional activity of a particular selected domain may be assessed in the context of the MHC class II polypeptides provided by this disclosure (e.g., the α1 polypeptides), for example T cell proliferation and/or CD74 binding assays.

Effective amount: A dose or quantity of a specified compound sufficient to inhibit advancement, or to cause regression of a disease or condition, or which is capable of relieving symptoms caused by the disease or condition. For instance, this can be the amount or dose of a disclosed MHC molecule required to treat or inhibit a disorder, such as an inflammatory and/or autoimmune disorder. In one embodiment, an effective amount is the amount that alone, or together with one or more additional therapeutic agents, induces the desired response in a subject, such as treating or inhibiting an inflammatory or autoimmune disorder or other disease or disorder.

Inflammation: A localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods well known in the art, such as the number of white blood cells, the number of polymorphonuclear neutrophils (PMN), a measure of the degree of PMN activation, such as luminal enhanced chemiluminescence, or a measure of the amount of cytokines present.

A primary inflammation disorder is a disorder that is caused by the inflammation itself. A secondary inflammation disorder is inflammation that is the result of another disorder. Inflammation can lead to a host of inflammatory diseases, including, but not limited to rheumatoid arthritis, osteoarthritis, inflammatory lung disease (including chronic obstructive pulmonary lung disease), inflammatory bowel disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis) and the like. Auto-immune disorders which include an inflammatory component (including, but not limited to multiple sclerosis) are also considered to be inflammatory disorders.

Inhibiting or treating a disease: "Inhibiting" a disease refers to inhibiting the full development of a disease, for example in a person who is known to have a predisposition to a disease such as an inflammatory or autoimmune disorder. Inhibition of a disease can span the spectrum from partial inhibition to substantially complete inhibition (prevention) of the disease for example in a subject who has a disease or disorder or is at risk of developing a disease or disorder. In some examples, the term "inhibiting" refers to reducing or delaying the onset or progression of a disease. A subject to be administered with an effective amount of the pharmaceutical compound to inhibit or treat the disease or disorder can be identified by standard diagnosing techniques for such a disorder, for example, basis of family history, or risk factor to develop the disease or disorder.

Linker A molecule that covalently links two molecules (such as two polypeptides). Linkers (such as a peptide linker or a chemical linker) may be included in the recombinant MHC polypeptides of the present disclosure for example between an α1 domain and an antigenic peptide. Peptide linker sequences, which are generally between 2 and 25 amino acids in length, are well known in the art and include, but are not limited to, the glycine(4)-serine spacer described by Chaudhary et al. (Nature 339:394-397, 1989). Similarly, chemical linkers (such as thiol bonds or crosslinking agents) are well known in the art.

MHC Class II: MHC class II molecules are formed from two noncovalently associated proteins, the α chain and the β chain. The α chain comprises α1 and α2 domains, and the β chain comprises β1 and β2 domains. The cleft into which the antigen fits is formed by the interaction of the α1 and β1 domains. The α2 and β2 domains are transmembrane Ig-fold like domains that anchor the α and β chains into the cell membrane of the APC. MHC class II complexes, when associated with antigen (and in the presence of appropriate co-stimulatory signals) stimulate CD4 T-cells. The primary functions of CD4 T-cells are to initiate the inflammatory response, to regulate other cells in the immune system, and to provide help to B cells for antibody synthesis.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21st 30 Edition (2005), describes compositions and formulations suitable for pharmaceutical delivery of the proteins herein disclosed.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated, phosphorylated, or ubiquinated forms.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Polypeptides or domains thereof that have a significant amount of sequence identity and function the same or similarly to one another—for example, the same protein in different species—can be called 'homologs.'

Methods of alignment of sequences for comparison are well known in the art. Various programs and alignment algorithms are described in: Smith & Waterman, *Adv. Appl. Math.* 2: 482, 1981; Needleman & Wunsch, *J. Mol. Biol.* 48: 443, 1970; Pearson & Lipman, *Proc. Natl. Acad. Sci. USA* 85: 2444, 1988; Higgins & Sharp, *Gene,* 73: 237-244, 1988; Higgins & Sharp, *Comput. Appl. Biosci.* 5: 151-153, 1989; Corpet et al., *Nucl. Acids Res.* 16, 10881-90, 1988; Huang et al., *Comput. Appl. Biosci.* 8, 155-65, 1992; and Pearson, *Methods Mol. Biol.* 24:307-331, 1994. Altschul et al. (*J. Mol. Biol.* 215:403-410, 1990) presents a detailed consideration of sequence alignment methods and homology calculations. The NCBI Basic Local Alignment Search Tool (BLAST) is available from several sources, including the National Center for Biotechnology Information (NCBI, Bethesda, Md.) and on the Internet, for use in connection with the sequence analysis programs blastp, blastn, blastx, tblastn and tblastx.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Subject: Living multi-cellular vertebrate organisms, a category that includes both human and non-human mammals.

III. DR-α Domains

Disclosed herein are isolated polypeptides which include an MHC class II α1 domain or fragment thereof and do not include MHC class II α2, β1, or β2 domains, but do include an antigenic peptide and a linker sequence. The amino acid sequences of mammalian MHC class II α chain proteins, as well as nucleic acids encoding these proteins, are well known in the art and available from numerous sources including GenBank. Exemplary sequences are provided in Auffray et al. (*Nature* 308:327-333, 1984) (human HLA DQ α); Das et al. (*Proc. Natl. Acad. Sci. USA* 80:3543-3547, 1983) (human HLA DR α); Lawrance et al. (*Nucl. Acids Res.* 13:7515-7528, 1985) (human HLA DP α); Syha et al. (*Nucl. Acids Res.* 17:3985, 1989) (rat RT1.B α); Benoist et al. (*Proc. Natl. Acad. Sci. USA* 80:534-538, 1983) (mouse I-A α); all of which are incorporated by reference herein. Additional MHC class II α polypeptides can be identified by one of ordinary skill in the art, for example, from public databases, such as the IMGT/HLA database (available on the world wide web at ebi.ac.uk/imgt/hla/).

In some embodiments, the disclosed polypeptides include an MHC class II α1 domain, such as a DR-α1, DP-α1, DQ-α1, DM-α1, or DO-α1 domain, or a portion thereof. In a particular embodiment, the MHC class II α1 domain is a human HLA-DRA polypeptide. The α1 domain is well defined in mammalian MHC class II α chain proteins. In some examples, MHC class II α chains include a leader sequence involved in trafficking the polypeptide that is proteolytically removed to produce the mature α polypeptide.

An α1 domain may include about amino acid residues 1-90 of the mature α chain, but one of ordinary skill in the art will recognize that the C-terminal cut-off of this domain is not necessarily precisely defined, and, for example, might occur at any point between amino acid residues 70-100 of the mature a chain. In some examples, the α1 domain includes amino acids 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, or 1-100 of a mature MHC class II α domain. In other examples, an α1 domain includes about residues 20-120 (such as about residues 20-110, 24-110, 24-109, 25-100, 25-109, 26-110, 26-109, 30-120, 32-120, 32-115, 26-90, 26-85, 26-84, or other overlapping regions) of a full length MHC class II α1 polypeptide. In some examples, the MHC class II α1 domain does not include an N-terminal methionine; however, an N-terminal methionine can be present, for example as a result of expression in a bacterial, yeast, or mammalian system.

In further examples, the α1 domain can include deletion or addition of a few amino acids at the 5'- and/or 3'-end, such as addition or deletion of about 1-10 amino acids, such as addition or deletion of 1, 2, 3, 4, 5, 6, 7, 8, 9, or 10 amino acids from the 5'- or 3'-end, or combinations thereof (such as a deletion from one end and an addition to the other end). The composition of the α1 domain may also vary outside of these parameters depending on the mammalian species and the particular a chain in question. One of ordinary skill in the art will appreciate that the precise numerical parameters of the amino acid sequence are less important than the maintenance of domain function (for example, CD74 binding or down-regulation).

In several embodiments, a recombinant polypeptide disclosed herein comprising an MHC class II α polypeptide, an antigenic peptide, and a linker includes, consists essentially of, or consists of the amino acid sequence set forth as SEQ ID NO: 1. In additional embodiments, the recombinant polypeptide has a sequence at least 75%, 85%, 90%, 95%, 96%, 97%, 98% or 99% identical to SEQ ID NO: 1 or a fragment thereof. For example, the polypeptide can be a homolog of SEQ ID NO: 1 with an amino acid sequence at least 85%, 90%, 95%, 96%, 97%, 98% or 99% identical to SEQ ID NO: 1 or a fragment thereof. Exemplary sequences can be obtained using computer programs that are readily available on the world wide web and the amino acid sequences set forth herein. In some examples, the homolog retains a function of the polypeptide of SEQ ID NO: 1 such as an altered secondary structure, binding to CD74, and inhibiting EAE.

Minor modifications of the recombinant polypeptide described as SEQ ID NO: 1 herein may result in polypeptides which have substantially equivalent activity as compared to SEQ ID NO: 1. Such modifications may be deliberate, as by site-directed mutagenesis, or may be spontaneous. All of the polypeptides produced by these modifications are included herein. Thus, a specific, non-limiting example of an MHC class II α1 polypeptide is a conservative variant of SEQ ID NO: 1 (such as a conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A list of exemplary conservative substitutions is provided above.

Nucleic acid molecules encoding SEQ ID NO: 1 and/or any homologs thereof can be produced by standard approaches, such as amplification by the polymerase chain reaction (PCR). Standard approaches for designing primers for amplifying open reading frames encoding the α1 domain and/or an antigenic peptide may be employed.

In some embodiments, SEQ ID NO: 1 and/or any homologs thereof can be expressed in prokaryotic or eukaryotic cells from a nucleic acid construct (such as a nucleic acid construct including SEQ ID NO: 2). Nucleic acid constructs expressing recombinant polypeptides may also include regulatory elements such as promoters, enhancers, and 3' regulatory regions, the selection of which will be determined based upon the type of cell in which the protein is to be expressed. The constructs are introduced into a vector suitable for expressing the recombinant polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), phage T7 and lambda $P_L$ promoters. Methods and plasmid vectors for producing heterologous proteins in bacteria or mammalian cells are described in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); and Ausubel et al., *Short Protocols in Molecular Biology: A Compendium of Methods from Current Protocols in Molecular Biology,* 4th ed., Wiley & Sons, 1999.

Suitable prokaryotic cells for expression of large amounts of proteins include *Escherichia coli* and *Bacillus subtilis.* Often, proteins expressed at high levels are found in insoluble inclusion bodies; methods for extracting proteins from these aggregates are described for example, by Sambrook et al. (2001, see chapter 15). Recombinant expression of recombinant polypeptides in prokaryotic cells may alternatively be conveniently obtained using commercial systems designed for optimal expression and purification of fusion proteins. Such fusion proteins typically include a tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). Additional systems include the His6-tag (e.g., Roche Applied Science, Mannheim, Germany) or streptavidin binding peptide (e.g., Sigma-Aldrich, St. Louis, Mo.). For example, the pMAL expression system utilizes a vector that adds a maltose binding protein to the expressed protein. The fusion protein is expressed in *E. coli.* and the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The recombinant polypeptides can also be expressed in eukaryotic expression systems, including *Pichia pastoris*, *Drosophila*, Baculovirus and/or Sindbis expression systems produced by Invitrogen (Carlsbad, Calif.). Eukaryotic cells such as Chinese Hamster ovary (CHO), monkey kidney (COS), HeLa, *Spodoptera frugiperda*, and *Saccharomyces cerevisiae* may also be used to express recombinant polypeptides. Regulatory regions suitable for use in these cells include, for mammalian cells, viral promoters such as those from CMV, adenovirus or SV40, and for yeast cells, the promoter for 3 phosphoglycerate kinase or alcohol dehydrogenase.

The transfer of DNA into eukaryotic cells is routine. The vectors are introduced into the recipient cells as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

An MHC class II α1 domain polypeptide produced in mammalian cells may be extracted following release of the protein into the supernatant and may be purified using an immunoaffinity column prepared using anti-MHC or other antibodies. Alternatively, the MHC polypeptide may be expressed as a chimeric protein with, for example, β-globin. Antibody to β-globin is thereafter used to purify the chimeric protein. Corresponding protease cleavage sites engineered between the β-globin gene and the nucleic acid sequence encoding the recombinant polypeptide are then used to separate the two polypeptide fragments from one another after translation. One useful expression vector for generating β-globin chimeric proteins is pSG5 (Stratagene, La Jolla, Calif.).

Expression of the recombinant polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells. In other examples, the recombinant polypeptide can be modified (for example, by site-directed mutagenesis) to include desired post-translational modification sites such as one or more sites for N-linked glycosylation, phosphorylation, or other modifications.

Purification of the expressed protein is generally performed in a basic solution (typically around pH 10) containing 6M urea. Folding of the purified protein is then achieved by dialysis against a buffered solution at neutral pH (typically phosphate buffered saline at around pH 7.4).

IV. Antigenic Peptides

The recombinant polypeptides disclosed herein comprise antigenic peptides covalently linked to the α1 domain—either directly or via a peptide linker. As is well known in the art (see for example U.S. Pat. No. 5,468,481) the presentation of antigen in MHC complexes on the surface of APCs generally does not involve a whole antigenic peptide. Rather, a peptide located in the groove between the β1 and α1 domains in the case of MHC II or the α1 and α2 domains in the case of MHC I is typically a small linear fragment of a whole polypeptide antigen. As discussed in Janeway & Travers (*Immunobiology: The Immune System in Health and Disease*, 1997), peptides located in the peptide groove of MHC class I molecules are constrained by the size of the binding pocket and are typically 8-15 amino acids long (such as 8, 9, 10, 11, 12, 13, 14, or 15 amino acids), more typically 8-10 amino acids in length (but see Collins et al., *Nature* 371:626-629, 1994 for possible exceptions). In contrast, peptides located in the peptide groove of MHC class II molecules are not constrained in this way and are often larger, typically at least 3-50 amino acids in length (such as 8-30, 10-25, or 15-23 amino acids in length). In some examples, the peptide located in the peptide groove of an MHC class II molecule is about 15-23 amino acids in length. Peptide fragments can be prepared by standard approaches, such as use of synthetic peptide synthesis machines or they can be expressed as part of a recombinant polypeptide.

In some examples, an antigenic peptide includes a peptide from a neuronal or central nervous system protein, such as a myelin protein (for example, myelin oligodendrocyte glycoprotein (MOG), myelin basic protein (MBP), or proteolipid protein (PLP)). In other examples, an antigenic determinant is a peptide from a retinal protein, such as interphotoreceptor retinoid binding protein (IRBP), arrestin, phosducin, or recoverin. Additional antigenic determinants include peptides from type II collagen (collagen II), fibrinogen-α, vimentin, α-enolase, human cartilage glycoprotein-39, α2 gliadin, or insulin. In some examples, an antigenic determinant includes a post-translational modification, such as phosphorylation, glycosylation, or citrullination. Sequences of exemplary antigenic determinants are provided for example in International Pat. Publ. No. WO 2012/103365 and U.S. Pat. Publ. No. 2012/0276127, both of which are incorporated herein by reference in their entirety. One of ordinary skill in the art can identify additional antigenic determinants relevant to a particular disease or disorder. In further examples the antigenic peptide includes a MOG-35-55 peptide, exemplified by amino acids 1-21 of SEQ ID NO: 1.

In some examples, the antigenic peptide is covalently linked to the MHC class II α1 polypeptide by operably linking a nucleic acid sequence encoding the selected antigenic peptide to the 5' end of the construct encoding the MHC class II α1 polypeptide such that, in the expressed peptide, the antigenic peptide is linked to the amino-terminus of the α1 domain. In other examples, the antigenic peptide is covalently linked to the MHC class II α1 polypeptide by operably linking a nucleic acid sequence encoding the selected antigen to the 3' end of the construct encoding the MHC class II α1 polypeptide such that, in the expressed peptide, the antigenic peptide is linked to the carboxy-terminus of the α1 domain. One convenient way of obtaining this result is to incorporate a sequence encoding the antigenic peptide into the PCR primers used to amplify the MHC class II α1 domain coding regions. In some examples, a sequence encoding a linker peptide sequence is included between the antigenic peptide and the MHC class II α1 polypeptide. However, it is not necessary that the antigenic peptide be ligated exactly at the 5' end (or 3' end) of the MHC class II α1 domain coding region. For example, the antigenic coding region may be inserted into the 1 domain within the first few (typically within the first 10) codons of the 5' or 3' end of the MHC class II α1 domain coding sequence.

In some embodiments, this genetic system for linkage of the antigenic peptide to the MHC class II α1 domain is particularly useful where a number of MHC class II α1 domains with differing antigenic peptides are to be produced. The described system permits the construction of an expression vector in which a unique restriction site is included in the MHC class II α1 domain (e.g., at the 5' or 3' end of the α1 domain). In conjunction with such a construct, a library of antigenic peptide encoding sequences is made, 
with each antigen-coding region flanked by sites for the selected restriction enzyme. The inclusion of a particular antigen into the MHC class II α1 domain is then performed simply by (a) releasing the antigen-coding region with the selected restriction enzyme, (b) cleaving the MHC class II α1 domain construct with the same restriction enzyme, and (c) ligating the antigen coding region into the MHC class II α1 domain construct. In this manner, a large number of MHC class II α1 domain-peptide antigen constructs can be made and expressed in a short period of time.

In some examples, the antigen is covalently linked to the MHC class II α1 domain polypeptide by a disulfide bond. In some examples, the disulfide linkage is formed utilizing a naturally occurring cysteine residue in the MHC class II α1 domain polypeptide (such as a cysteine residue in the MHC class II α1 domain). One of ordinary skill in the art can identify a suitable cysteine residue in an MHC class II α1 domain polypeptide. In other examples, the disulfide linkage is formed utilizing a non-naturally occurring cysteine residue in the MHC class II α1 domain polypeptide, such as a cysteine residue introduced in the MHC class II α1 domain polypeptide by mutagenesis. In further examples, the disulfide linkage is formed utilizing a naturally occurring cysteine residue in the peptide antigen. In still further examples, the disulfide linkage is formed utilizing a non-naturally occurring cysteine residue in the peptide antigen, such as a cysteine residue introduced in the peptide antigen by mutagenesis.

V. Methods of Treating or Inhibiting Disorders

Disclosed herein are methods of treating or inhibiting disorders in a subject, including but not limited to inflammatory and/or autoimmune disorders. The disclosed methods include administering a recombinant polypeptide comprising an MHC class II α1 domain polypeptide covalently linked to an antigen through a linker (exemplified by SEQ ID NO: 1) to a subject.

In some embodiments, the methods include selecting a subject with a disorder for treatment and administering an effective amount of the recombinant polypeptide described herein or a nucleic acid encoding the recombinant polypeptide described herein to the subject.

In some embodiments, the subject has an inflammatory and/or autoimmune disease or disorder, including but not limited to, systemic lupus erythematosus, Sjogren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, celiac disease, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Ban virus infection, rubulavirus, and Evan's syndrome.

Additional inflammatory diseases include osteoarthritis, inflammatory lung disease (including chronic obstructive pulmonary lung disease), periodontal disease, polymyalgia rheumatica, atherosclerosis, systemic sclerosis, allergic rhinitis, and skin disorders (including dermatomyositis and psoriasis) and the like.

In other embodiments, the subject has a retinal disorder, such as a retinal degeneration, such as retinitis pigmentosa, cone-rod dystrophy, Leber congenital amaurosis, or a maculopathy (for example, age-related macular degeneration, Stargardt-like macular degeneration, vitelliform macular dystrophy (Best disease), Malattia Leventinese (Doyne's honeycomb retinal dystrophy), diabetic maculopathy, occult macular dystrophy, and cellophane maculopathy). In other examples, a retinal disorder includes a retinopathy, such as autoimmune retinopathy, diabetic retinopathy, or vascular retinopathy. In still further examples, a retinal disorder includes retinal detachment or glaucoma. Retinal disorders may be progressive (for example, retinal degeneration or glaucoma) or acute (for example, retinal detachment). In additional examples, the subject is a subject with uveitis or optic neuritis. In other embodiments, the subject has had a stroke (such as ischemic stroke or hemorrhagic stroke). In still further examples, the subject is a subject with substance addiction, for example, a subject with cognitive or neuropsychiatric impairment induced by substance addiction including methamphetamine and alcohol abuse.

In some embodiments, a subject is administered an effective amount of a composition including an MHC class II α1 domain or a portion thereof (such as a portion of an α1 domain which is capable of binding CD74 or decreasing expression and/or activity of CD74). In one example, the composition includes DRα1-MOG-35-55 (for example, SEQ ID NO: 1). Pharmaceutical compositions that include the recombinant polypeptide disclosed herein can be formulated with an appropriate solid or liquid carrier, depending upon the particular mode of administration chosen. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21st Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate.

In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations. The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition may be administered by any mode that achieves its intended purpose. Amounts and regimens for the administration of the recombinant polypeptides or portion thereof (or a nucleic acid encoding such polypeptides) can be determined by the attending clinician. Effective doses for therapeutic application will vary depending on the nature and severity of the condition to be treated, the particular MHC class II α1 domain or portion thereof selected, the age and condition of the patient, and other clinical factors. Typically, the dose range will be from about 0.1 µg/kg body weight to about 100 mg/kg body weight. Other suitable ranges include doses of from about 100 µg/kg to about 50 mg/kg body weight, about 500 µg/kg to about 10 mg/kg body weight, or about 1 mg/kg to about 5 mg/kg body weight. The dosing schedule may vary from once a week to daily depending on a number of clinical factors, such as the subject's sensitivity to the protein. Examples of dosing schedules are about 1 mg/kg administered once a month, bi-weekly, once a week, twice a week, three times a week or daily; a dose of about 2.5 mg/kg once a week, twice a week, three times a week or daily; a dose of about 5 mg/kg once a week, twice a week, three times a week or daily; a dose of about 10 mg/kg once a week, twice a week, three times a week or daily; or a dose of about 30 mg/kg once a week, twice a week, three times a week or daily.

The pharmaceutical compositions that include one or more of the disclosed recombinant polypeptides can be formulated in unit dosage form, suitable for individual administration of precise dosages. In one specific, non-limiting example, a unit dosage can contain from about 1 ng to about 5 g of the recombinant polypeptide (such as about 10 µg to 1 g, about 100 mg to 500 mg, or about 10 mg to 100 mg). The amount of active compound(s) administered will be dependent on the subject being treated, the severity of the affliction, and the manner of administration. Within these bounds, the formulation to be administered will contain a quantity of the active component(s) in amounts effective to achieve the desired effect in the subject being treated.

The recombinant polypeptides can be administered to humans or other animals on whose tissues they are effective in various manners such as topically, orally, intravenously, intramuscularly, intraperitoneally, intranasally, intradermally, intrathecally, subcutaneously, intraocularly, via inhalation, or via suppository. In one example, the compounds are administered to the subject subcutaneously. In another example, the compounds are administered to the subject intravenously.

In some embodiments, the recombinant polypeptides can be included in an inert matrix for topical application. In some examples, the formulation can be injected into the eye, for example for intravitreal injection. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including one or more recombinant polypeptides can be applied topically, either in the form of drops or as an aqueous based cream, or can be injected intraocularly. In a formulation for topical application, the recombinant polypeptide is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the recombinant polypeptide over time. In one example, the MHC class II α1 domain can be dissolved in an organic solvent such as DMSO or alcohol as previously described and contain a polyanhydride, poly(glycolic) acid, poly(lactic) acid, or polycaprolactone polymer. The recombinant polypeptide can be included in a delivery system that can be implanted at various sites in the eye, depending on the size, shape and formulation of the implant, and the type of transplant procedure. Suitable sites include but are not limited to the anterior chamber, anterior segment, posterior chamber, posterior segment, vitreous cavity, suprachoroidal space, subconjunctiva, episcleral, intracorneal, epicorneal and sclera.

In some examples, an effective amount (for example, a therapeutically effective amount) of a disclosed recombinant polypeptide can be the amount of recombinant polypeptide necessary to treat or inhibit a disorder (such as an inflammatory and/or autoimmune disorder) in a subject. In other examples, a therapeutically effective amount of a disclosed recombinant polypeptide can be the amount of recombinant polypeptide necessary to treat or inhibit a retinal disorder, stroke, or disorders associated with substance addiction (such as cognitive or neuropsychiatric impairment resulting from substance addiction).

The present disclosure also includes combinations of one or more of the disclosed recombinant polypeptides with one or more other agents useful in the treatment of a disorder. In some examples, the recombinant polypeptides can be administered with effective doses of one or more therapies for inflammatory or autoimmune disorders, including but not limited to non-steroidal anti-inflammatory drugs, corticosteroids, methotrexate, anti-TNF compounds, mycopheonlate, aminoslicylates, antibiotics, interferons, glatiramer acetate, antibody therapies (such as rituximab or milatuzumab), or immunosuppressant or immunomodulator compounds. In another example, the recombinant polypeptides can be administered in combination with effective doses of one or more therapies for retinal disorders, including but not limited to, gene therapy, vitamin or mineral supplements (such as vitamins A, C, and/or E, or zinc and/or copper), anti-angiogenic therapy (such as ranibizumab or bevacizumab), photocoagulation, photodynamic therapy, lutein or zeaxanthin, cortico steroids, or immunosuppressants. Appropriate combination therapy for a particular disease can be selected by one of ordinary skill in the art. The term "administration in combination" or "co-administration" refers to both concurrent and sequential administration of the active agents.

EXAMPLES

The following examples are illustrative of disclosed methods. In light of this disclosure, those of skill in the art will recognize that variations of these examples and other examples of the disclosed method would be possible without undue experimentation.

Example 1

Figure 1:
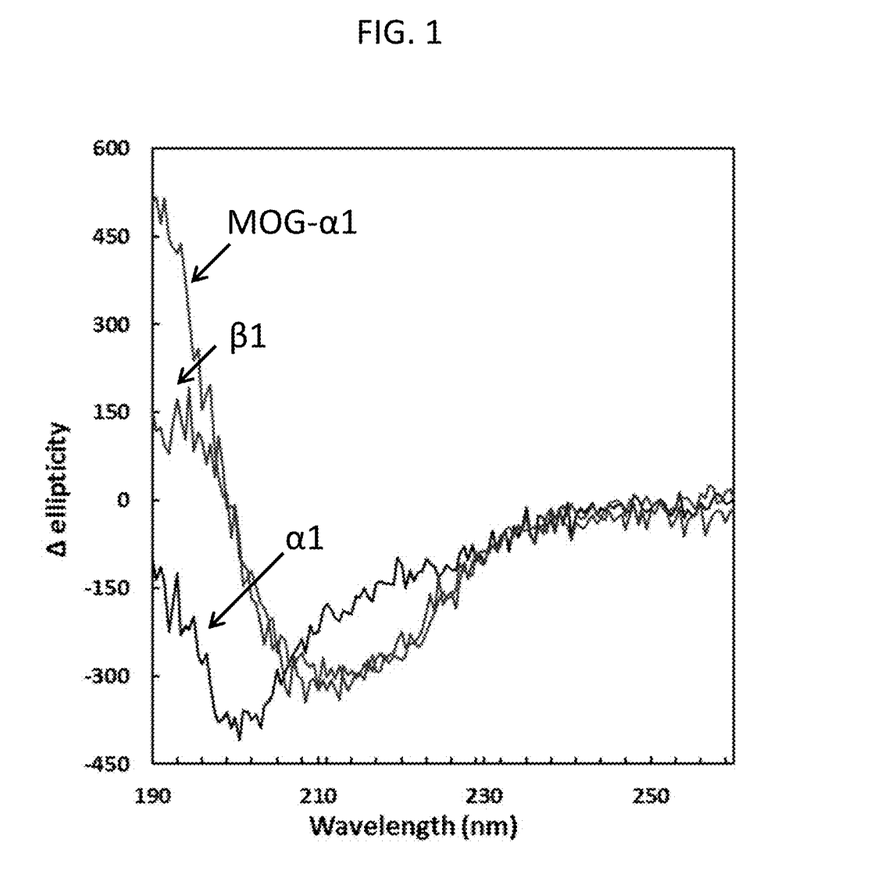
FIG. 1 is a plot depicting the far UV spectra of an α1 domain, β1 domain, and MOG-α1 domain (SEQ ID NO: 1) constructs in 20 mM Tris, pH 8.5 at a concentration of 1 mg/ml. Spectra were taken on an AVIV spectropolarimeter at 0.5 nm intervals using a 0.1 cm light path.

Inclusion of the Amino Terminus Peptide Extension Confers Secondary Structure to the DRα1-MOG-35-55 Construct Not Present in DRα1 Alone Circular dichroism (CD) analysis was performed on DRα1-MOG-35-55, DRα1 and DR2β1 to evaluate secondary structure. The results demonstrated probable secondary structure (both alpha helix and beta sheet) present in the DRα1-MOG-35-55 construct that was not present in the DRα1 construct without the peptide extension. The results are shown in FIG. 1.

Example 2

Figure 2:
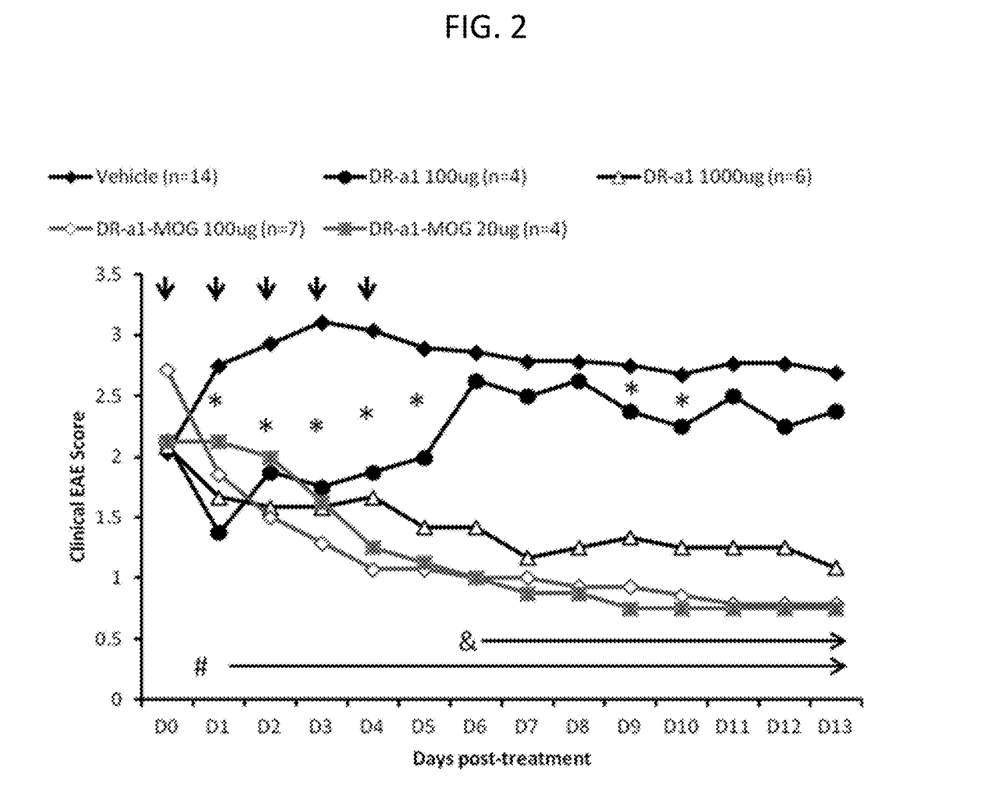
FIG. 2 is a line graph depicting the daily mean clinical EAE scores for groups of DR*1501 mice subjected to the EAE model described in WO 2013/103816 and given the indicated treatments on five consecutive days (indicated by arrows). DR-α1 MOG is SEQ ID NO: 1. *—$p<0.05$, #—$p<0.001$, &—$p<0.03$ as analyzed by a Mann Whitney U test.
Figure 3:
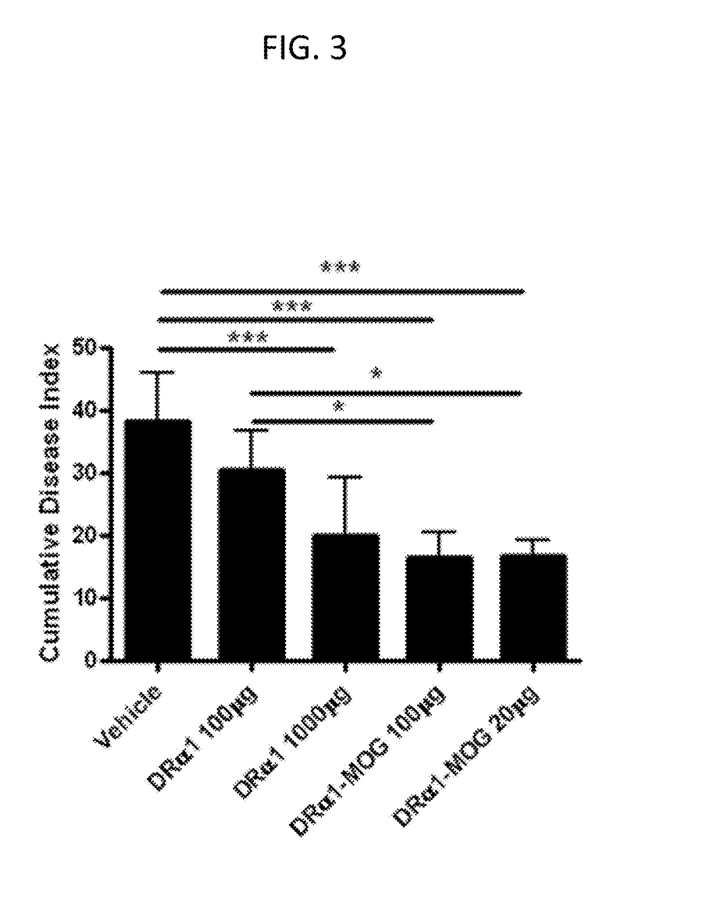
FIG. 3 is a bar graph of cumulative disease index for the groups described in FIG. 2. *—$p<0.05$, ***—$p<0.001$ as analyzed by a one way ANOVA with Tukey post-test.
Figure 4A:
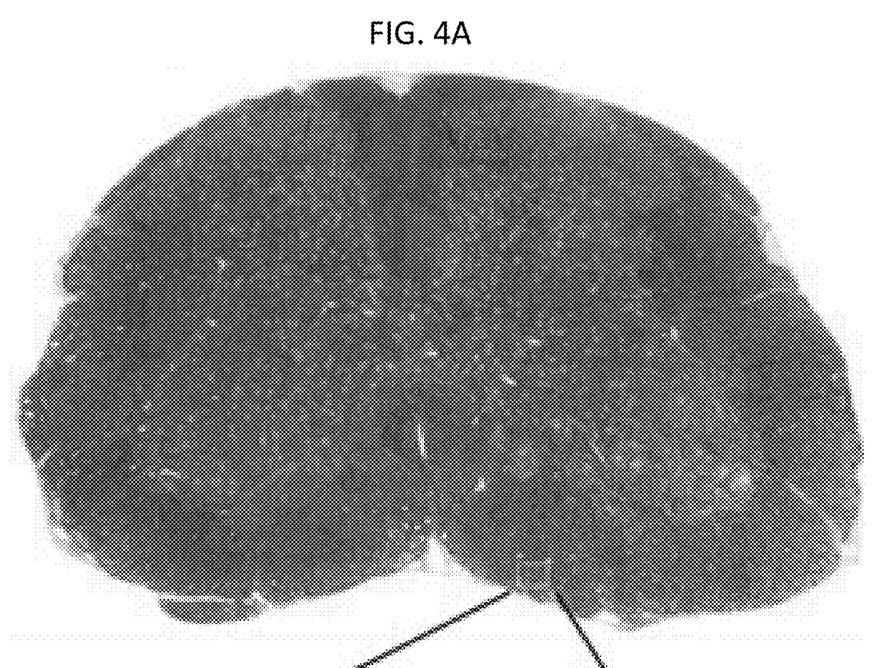
FIG. 4A is a low power image of the spinal cord of a vehicle treated mouse.
Figure 4B:
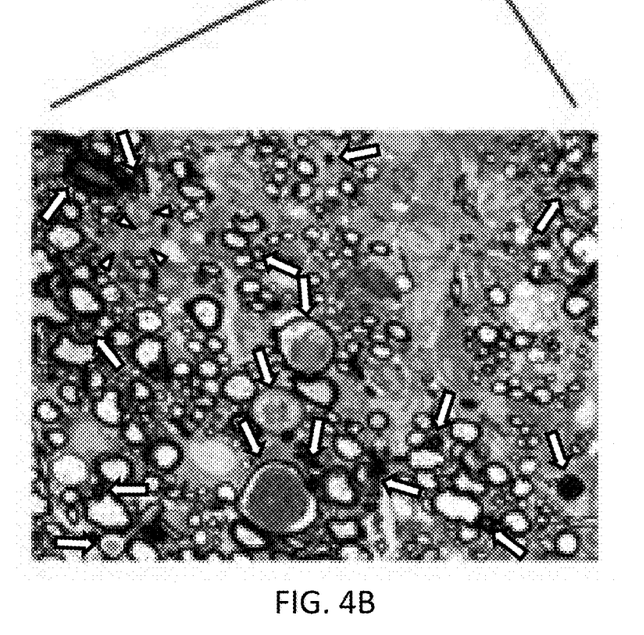
FIG. 4B is a representative area of tissue damage from a vehicle treated mouse.
Figure 4C:
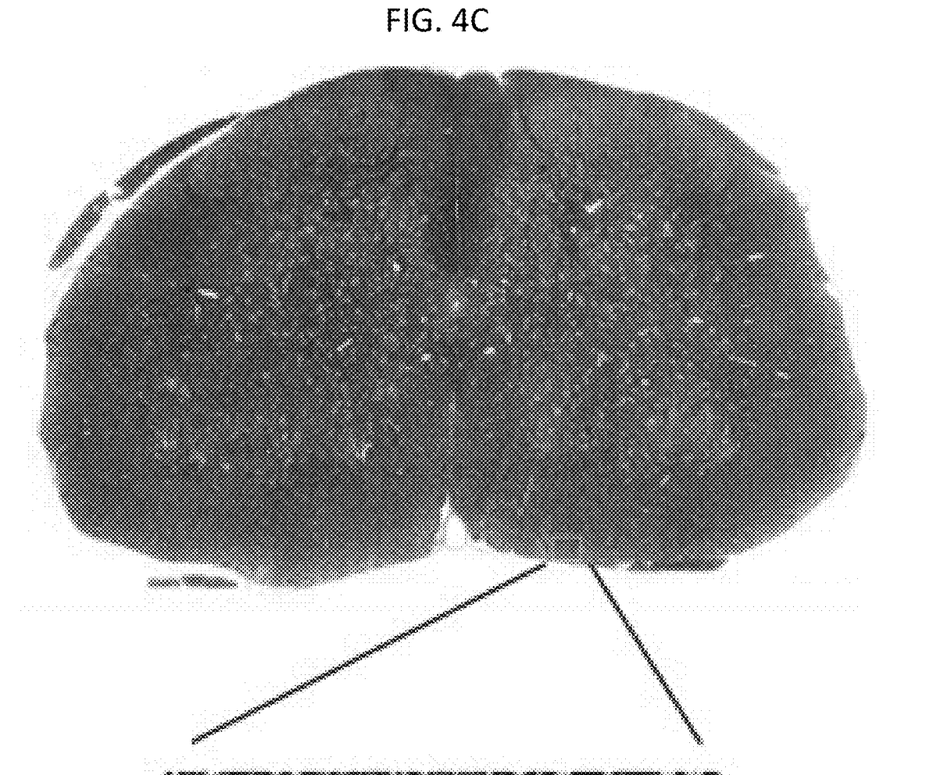
FIG. 4C is a low power image of the spinal cord of a mouse treated with SEQ ID NO: 1.
Figure 4D:
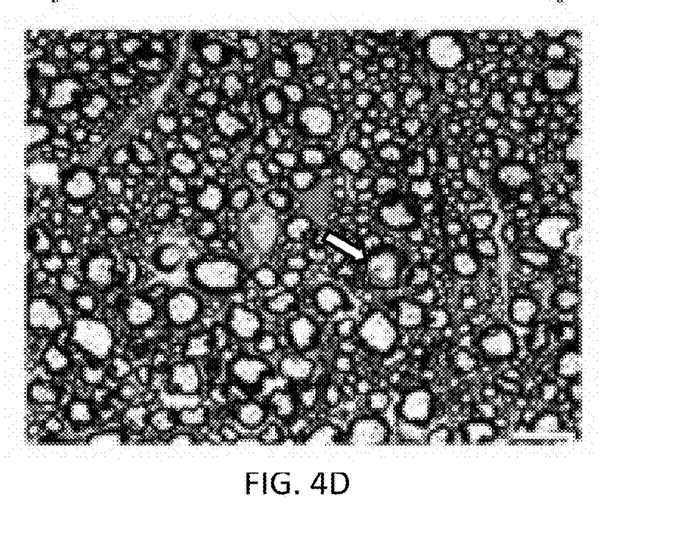
FIG. 4D is a representative area of a similar section from a mouse treated with SEQ ID NO: 1. White rectangles indicate areas of magnification. Arrows indicate demyelinated axons. Note also increased density of axons and reduced cellular infiltration in the SEQ ID NO: 1 treated mice.

DRα1-MOG-35-55 Treats Clinical and Histological EAE with >50 Fold Greater Potency than a DRα1-MOG-35-55 Lacking the Peptide To evaluate biological activity, the DRα1-MOG-35-55 was compared to DRα1 alone in treating clinical and histological signs of experimental autoimmune encephalomyelitis (EAE) in DR2-Tg mice. As is shown in FIGS. 2 and 3, mice treated at onset of disease with DRα1-MOG-35-55 (20 µg/day×5 days) showed a significant reduction of clinical and histological signs compared to Vehicle treated mice, whereas a 50-fold higher dose (1,000 µg/day×5 days) showed less efficacy than DRα1-MOG-35-55 normalized to the vehicle control. As is shown in FIGS. 4A-4D, the DRα1-MOG-35-55 construct also strongly inhibited histological signs of EAE in the spinal cord, including lower infiltration of inflammatory T-cells and macrophages and less axonal damage and demyelination. Treatment with DRα1-MOG-35-55 reduced total damage in the ventral region by 95% and in the dorsal region by 93%.

Example 3

Figure 5:
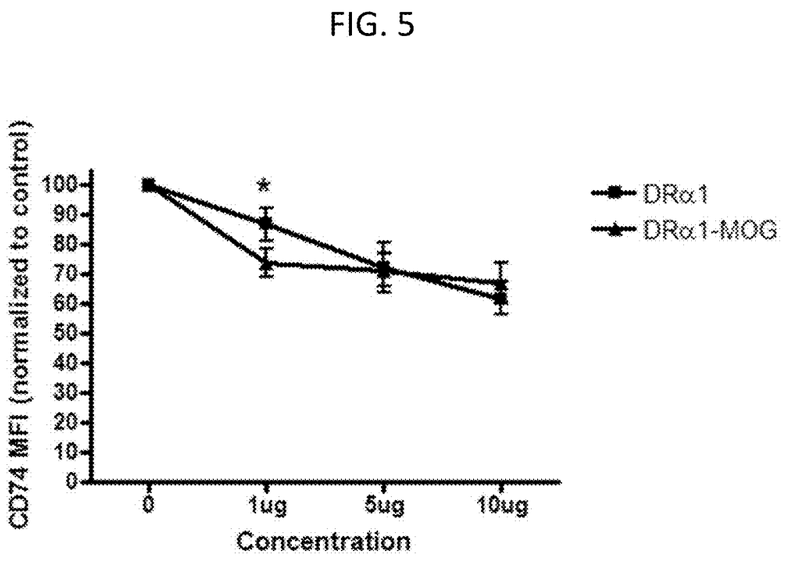
FIG. 5 shows PBMC from human healthy control (HC) subjects (n=3) that are incubated with DRα1 or DRα1-MOG-35-55 at different concentrations (1 μg, 5 μg, 10 μg) or were untreated (0 μg). CD11b+ monocytes are analyzed for CD74 expression (CD74 MFI are normalized to the untreated sample as 100% of each subject). *$p<0.05$, Student's t-test.

DRα1-MOG-35-55 is More Potent than DRα1 Alone in Down-Regulating of CD74 on Human CD11b+ Monocytes DRα1 and DRα1-MOG-35-55 are believed to act through the down-modulation of expression of CD74 on monocytes, thereby reducing the availability of this receptor for macrophage migration inhibitory factor, MIF, on the cell surface. FIG. 5 shows that treatment with the DRα1-MOG-35-55 construct results in a significantly enhanced down-regulation of CD74 than DRα1 alone when 1 µg of each construct was incubated for 1 hour with CD11b$^+$ splenocytes.

---

We claim:

1. A recombinant polypeptide comprising a Drα1 domain, an antigenic peptide, and a linker sequence, said linker sequence comprising a first glycine-serine spacer, a thrombin cleavage site and a second glycine-serine spacer, wherein the recombinant polypeptide does not comprise MHC Class II α2, β1, and β2 domains.

2. The recombinant polypeptide of claim 1, wherein the antigenic peptide is mouse or human MOG-35-55.

3. The recombinant polypeptide of claim 2, wherein the recombinant polypeptide comprises SEQ ID NO: 1.

4. The recombinant polypeptide of claim 3, wherein the recombinant polypeptide consists of SEQ ID NO: 1.

5. A composition comprising an effective dose of the recombinant polypeptide of claim 1 and a pharmaceutically acceptable carrier.

6. The composition of claim 5, wherein the dose is at least 5 mg/kg.

7. A method of treating multiple sclerosis or experimental autoimmune encephalopathy (EAE), comprising administering a recombinant polypeptide comprising a DRα1 domain, a mouse or human MOG-35-55 antigenic peptide, and a linker sequence, said linker sequence comprising a first glycine-serine spacer, a thrombin cleavage site and a second glycine-serine spacer, wherein the recombinant polypeptide does not comprise MHC Class II α2, β1, and β2 domains to a subject with multiple sclerosis or EAE.

8. The method of claim 7, wherein the recombinant polypeptide comprises or consists of SEQ ID NO: 1.

* * * * *

SEQUENCE LISTING

<160> NUMBER OF SEQ ID NOS: 2

<210> SEQ ID NO 1
<211> LENGTH: 120
<212> TYPE: PRT
<213> ORGANISM: Artificial Sequence
<220> FEATURE:
<223> OTHER INFORMATION: DRa1 polypeptide linked to MOG35-55

<400> SEQUENCE: 1

```
Met Glu Val Gly Trp Tyr Arg Ser Pro Phe Ser Arg Val Val His Leu
1               5                   10                  15

Tyr Arg Asn Gly Lys Gly Gly Gly Ser Leu Val Pro Arg Gly Ser
            20                  25                  30

Gly Gly Gly Gly Ile Lys Glu Glu His Val Ile Ile Gln Ala Glu Phe
        35                  40                  45

Tyr Leu Asn Pro Asp Gln Ser Gly Glu Phe Met Phe Asp Phe Asp Gly
    50                  55                  60

Asp Glu Ile Phe His Val Asp Met Ala Lys Lys Glu Thr Val Trp Arg
65                  70                  75                  80

Leu Glu Glu Phe Gly Arg Phe Ala Ser Phe Glu Ala Gln Gly Ala Leu
                85                  90                  95
```

```
Ala Asn Ile Ala Val Asp Lys Ala Asn Leu Glu Ile Met Thr Lys Arg
            100                 105                 110

Ser Asn Tyr Thr Pro Ile Thr Asn
        115                 120

<210> SEQ ID NO 2
<211> LENGTH: 363
<212> TYPE: DNA
<213> ORGANISM: Artificial Sequence
<220> FEATURE:
<223> OTHER INFORMATION: nucleic acid encoding a DRa1 polypeptide linked
      to MOG35-55

<400> SEQUENCE: 2
atggaagttg gttggtaccg ttccccgttc tcccgtgttg ttcacctgta ccgtaacggt      60
aaaggaggtg gaggctcact agtgccccga ggctctggag gtggaggcat caaagaagaa     120
catgtgatca tccaggccga gttctatctg aatcctgacc aatcaggcga gtttatgttt     180
gactttgatg gtgatgagat tttccatgtg gatatggcaa agaaggagac ggtctggcgg     240
cttgaagaat ttggacgatt tgccagcttt gaggctcaag gtgcattggc aacatagct     300 gtggacaaag ccaacttgga aatcatgaca aagcgctcca actatactcc gatcaccaat     360
taa                                                                   363
```

UNITED STATES PATENT AND TRADEMARK OFFICE
CERTIFICATE OF CORRECTION

PATENT NO. : 10,316,075 B2
APPLICATION NO. : 14/506502
DATED : June 11, 2019
INVENTOR(S) : Vandenbark et al.

Page 1 of 1

It is certified that error appears in the above-identified patent and that said Letters Patent is hereby corrected as shown below:

In the Specification

Column 1, Line 14, "This invention was made with the support of the United States government under the terms of Grant Number 5RO1 NS047661 awarded by the National Institutes of Health and a Merit Review Grant awarded by the Veterans Administration. The United States government has certain rights to this invention." should read --This invention was made with government support under NS047661 and AI043960 awarded by the National Institutes of Health. The government has certain rights in the invention.--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*